United States Patent
Spena et al.

(10) Patent No.: US 12,116,404 B2
(45) Date of Patent: Oct. 15, 2024

(54) antiRPS4Y1 mAb

(71) Applicants: Fondazione IRCCS Ca' Granda—Ospedale Maggiore Policlinico, Milan (IT); Fondazione Luigi Villa, Milan (IT)

(72) Inventors: Silvia Spena, Trezzano sul Naviglio (IT); Flora Peyvandi, Milan (IT)

(73) Assignees: FONDAZIONE IRCCS CA'GRANDA-OSPEDALE MAGGIORE POLICILINICO, Milan (IT); FONDAZIONE LUIGI VILLA, Milan (IT)

( * ) Notice: Subject to any disclaimer, the term of this patent is extended or adjusted under 35 U.S.C. 154(b) by 0 days.

(21) Appl. No.: 17/673,912

(22) Filed: Feb. 17, 2022

(65) Prior Publication Data

US 2023/0257450 A1 Aug. 17, 2023

(51) Int. Cl.
*C07K 16/18* (2006.01)
*G01N 33/68* (2006.01)

(52) U.S. Cl.
CPC ............ *C07K 16/18* (2013.01); *G01N 33/689* (2013.01); *C07K 2317/34* (2013.01); *G01N 2800/385* (2013.01)

(58) Field of Classification Search
None
See application file for complete search history.

(56) References Cited

PUBLICATIONS

Hoch et al., Sex matters: XIST and DDX3Y gene expression as a tool to determine fetal sex in human first trimester placenta. Placenta 97 (2020) 68-70 (Year: 2020).*
Edwards et al., The remarkable flexibility of the human antibody repertoire; isolation of over one thousand different antibodies to a single protein, BLyS. J Mol Biol. Nov. 14, 2003;334(1):103-18. (Year: 2003).*
Lo et al., Presence of fetal DNA in maternal plasma and serum, Lancet, 350:485-87 (1997).
Devaney et al., Noninvasive Fetal Sex Determination Using Cell-Free Fetal DNA:, JAMA, 306(6): 627-636 (2011).
Zadeh et al., Evaluation of an Improved Non-invasive Fetal Sex Determination in Haemophilia A Patients, Journal of Clinical and Diagnostic Research, 9(7): GC01-GC04 (2015).
Bowna-Smart et al., Sex selection and non-invasive prenatal testing: A review of current practices, evidence, and ethical issues, Prenatal Diagnosis. 40:398-407 (2020).

(Continued)

*Primary Examiner* — Aurora M Fontainhas
(74) *Attorney, Agent, or Firm* — BROWDY AND NEIMARK, PLLC

(57) ABSTRACT

It forms an object of the present invention a monoclonal antibody or an antigen-binding fragment thereof, which specifically binds to RPS4Y1 protein, preferably to human RPS4Y1, recognizing an epitope comprising sequence Y1 (SEQ ID NO: 3), and/or sequence Y2 (SEQ ID NO: 4) and/or sequence Y3 (SEQ ID NO: 5) of RPS4Y1.
In a further embodiment, it is here claimed a non-invasive method to identify male foetal cells within three months of gestation, said method comprising detecting the presence of RPS4Y1 protein in a maternal biological tissue sample by an antibody or an antigen-binding fragment thereof, according to the present invention.

4 Claims, 5 Drawing Sheets

Figure 1:
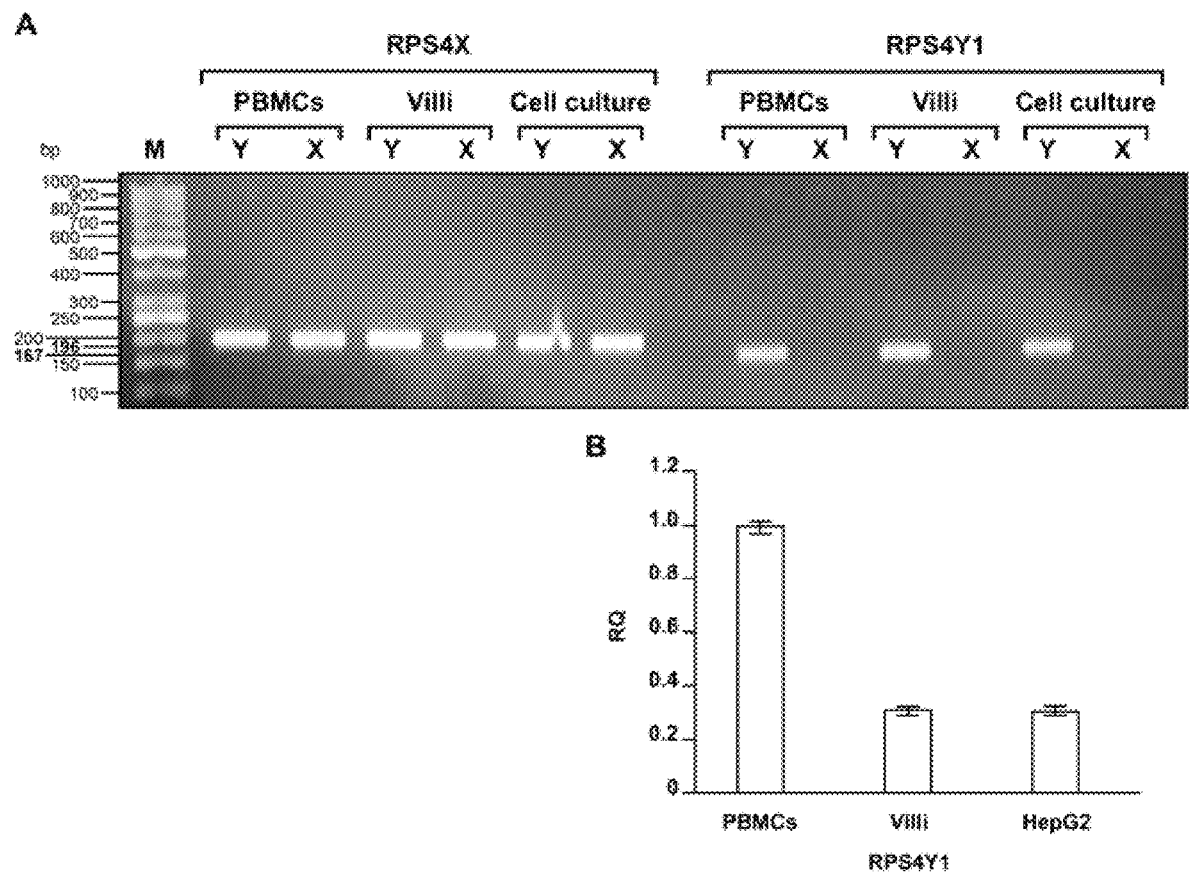

Specification includes a Sequence Listing.

(56) References Cited

PUBLICATIONS

Tsui et al., Noninvasive prenatal diagnosis of hemophilia by microfluidics digital PCR analysis of maternal plasma DNA, Blood, 117(13):3684-3691 (2011).
Hudecova et al., Noninvasive detection of F8 int22h-related inversions and sequence variants in maternal plasma of hemophilia carriers, BLOOD, 130(3):340-347 (2017).
Chen et al., Noninvasive prenatal diagnosis of hemophilia A by a haplotype-based approach using cell-free fetal DNA,68(3):117-121 (2020).
Fiddler, Fetal cell based prenatal diagnosis: Perspectives on the present future, J. Clin. Med., 3:972-985 (2014).
Mergenthaler et al., FISH Analysis of All Fetal Nucleated Cells in Maternal Whole Blood: Improved Specificity by the Use of Two Y-chromosome Probes, Journal of Histochemistry & Cytochemistry, 53(3): 319-322, (2005).
Rezaei et al., A Reappraisal of Circulating Fetal Cell Noninvasive Prenatal Testing, Trends in Biotechnology, 37 (6):632-644 (2019).
Ganshirt-Ahlert et al., Magnetic cell sorting and the transferrin receptor as potential means of prenatal diagnosis from maternal blood, 166:1350-1355 (1992).
Bianchi et al., Erythroid-specific antibodies enhance detection of fetal nucleated erythrocytes in maternal blood, 13:293-300 (1993).
Mavrou et al., Identification of Fetal Nucleated Red Blood Cells in the Maternal Circulation during Pregnancy Using Anti-Hemoglobin-Antibody, Fetal Diagn Ther, 18:309-313 (2003).
Sekizawa et al., Development of noninvasive fetal DNA diagnosis from nucleated erythrocytes circulating in maternal blood, Prenat Diagn, 27: 846-848 (2007).
Zimmermann et al., Unique monoclonalantibodiesspecifically bindsurface structures onhumanfetalerythroidbloodcells, Experimental Cell Research, 319:2700-2707 (2013).
Chang et al., A novel method for noninvasive diagnosis of monogenic diseases from circulating fetal cells, Prenatal Diagnosis. 41:400-408. (2021).
Hatt et al., Characterization of Fetal Cells from the Maternal Circulation by Microarray Gene Expression Analysis—Could the Extravillous Trophoblasts Be a Target for Future Cell-Based Non-Invasive Prenatal Diagnosis?, Fetal Diagn Ther, 35:218-227 (2014).
Kolvraa et al., Genome-wide copy number analysis on DNA from fetal cells isolated from the blood of pregnant women. pp. 1-26, (2016).
Brinch et al., Identification of circulating fetal cell markers by microarray analysis, Prenatal Diagnosis , 32, 742-751 (2012).
Zinn et al., Structure and Function of Ribosomal Protein S4 Genes on the Human and Mouse Sex Chromosomes, Molecular and Cellular Biology, 2485-2492 (1994).
Lopes et al., RTehseaerc hh aurticmle an RPS4 paralogue on Yq11.223 encodes a structurally conserved ribosomal protein and is preferentially expressed during spermatogenesis, BMC Molecular Biology, 11:33 (2010).
Shah et al., Do you know the sex of your cells?, Am J Physiol Cell Physiol 306: C3-C18, (2014).
English translation of the certificate of deposit of microorganism dated Feb. 6 and 7, 2022.
Spena et al., Development of a Specific Monoclonal Antibody to Detect Male Cells Expressing the RPS4Y1 Protein, Int. J. Mol. Sci., pp. 1-14 (2021).

* cited by examiner

```
                                                                X1/Y1
RPS4X_P62701    MARGPKKHLKRVAAPKHWMLDKLTGVFAPRPSTGPHKLRECLPLIIFLRNRLKYALTGDE 60
RPS4Y1_P22090   MARGPKKHLKRVAAPKHWMLDKLTGVFAPRPSTGPHKLRECLPLIVFLRNRLKYALTGDE 60
                                                *
                                                                X1/Y1
RPS4X_P62701    VKKICMQRFIKIDGKVRTDITYPAGFMDVISIDKTGENFRLIYDTKGRFAVHRITPEEAK 120
RPS4Y1_P22090   VKKICMQRFIKIDGKVRVDVTYPAGFMDVISIEKTGEHFRLVYDTKGRFAVHRITVEEAK 120
                                 *  *            *    *   *                *
                    X2/Y2                              X3/Y3
RPS4X_P62701    YKLCKVRKIFVGTKGIPHLVTHDARTIRYPDPLIKVNDTIQIDLETGKITDFIKFDTGNL 180
RPS4Y1_P22090   YKLCKVRKITVGVKGIPHLVTHDARTIRYPDPVIKVNDTVQIDLGTGKIINFIKFDTGNL 180
                         * *                     *      *    *    **   **

RPS4X_P62701    CMVTGGANLGRIGVITNRERHPGSFDVVHVKDANGNSFATRLSNIFVIGKGNKPWISLPR 240
RPS4Y1_P22090   CMVIGGANLGRVGVITNRERHPGSFDVVHVKDANGNSFATRLSNIFVIGNGNKPWISLPR 240
                   *       *                                     *

RPS4X_P62701    GKGIRLTIAEERDKRLAAKQSSG 263
RPS4Y1_P22090   GKGIRLTVAEERDKRLATKQSSG 263
                       *         *
```

Fig. 2 antiRPS4Y1 mAb

The Sequence Listing in ASCII text file format of 6,625 bytes in size, created on Apr. 21, 2022, with the file name "2022-04-25SequenceListing_SPENA1," filed in the U.S. Patent and Trademark Office on even date herewith, is hereby incorporated herein by reference.

BACKGROUND

In pregnant women carriers of X-linked recessive congenital disorder, prenatal diagnosis is useful to prepare the family and to plan the delivery and is usually offered when pregnancy termination would be considered in case of an affected foetus. The current guidelines state that foetal sex can be determined early (from 7 weeks of gestation) by a non-invasive prenatal test (NIPT) based on analysis of cell free foetal DNA (cffDNA), small (100-150 bp) fragments of DNA released from apoptotic placental cells circulating in the maternal blood [1], through the amplification of Y-linked markers (SRY, DYS14) [2,3]. NIPT for foetal sex determination is currently being adopted in health care systems across the world [4]. However, due to the poor cffDNA quantity and the high maternal DNA contamination (>90%), NIPT cannot be applied for the diagnosis of X-linked inherited diseases, such as haemophilia [5-7]. Hence, in case of a male foetus at risk, conventional invasive diagnostic procedures such as chorionic villus sampling and amniocentesis, with the associated risk of miscarriage, are mandatory to identify in foetuses the maternally inherited genetic defect.

As cffDNA, foetal cells (i.e., trophoblastic cells, nucleated red blood cells, granulocytes, lymphocytes, and hematopoietic stem cells) [8] circulate in the maternal blood in number of 4-36 cells/mL [9]. As source of whole foetal genome, circulating foetal cells are an ideal target for NIPT with a potential wider diagnostic range than cffDNA. Nevertheless, the lack of validated and highly specific foetal biomarkers, enabling the unambiguous identification of foetal cells, has been the most limiting factor in all developed strategies for their isolation [10].

To isolate foetal nucleated red blood cells, several antigens highly but not uniquely expressed in erythroid precursors have been tagged such as CD71 [11], glycophorin A [12], γ-hemoglobin [13], and N-acetylgalactosamine residues [14]. A specific antibody for a novel surface antigen of foetal erythroblast cells has been recently reported [15]. Similarly, a cocktail of antibodies against endothelial [16] and epithelial markers expressed in circulating endovascular trophoblasts has been developed for their enrichment and staining, respectively [17,18]. Moreover, the protein products of MMP14, MCAM, KCNQ4, CLDN6, and F3 genes, expressed in foetal cells, have been proposed as suitable surface markers for foetal cell enrichment [19]. Despite advances in the enrichment technologies based on large size (>15 μm) of trophoblastic cells, such as isolation of epithelial tumor/trophoblast by filtration and density gradient methods, isolation of foetal cells for clinical implementation remains a technical challenge.

Ribosomal Protein S4 Y-linked 1 (RPS4Y1) was found in transcriptionally active ribosomes extracted from placenta of a male foetus [20] and expressed in testis and in several somatic tissues of male individuals [21]. However, specific monoclonal antibodies against RPS4Y1 are not available so far.

There is an unmet need for early stage, non-invasive and accurate methods to identify male foetal cells for a non-invasive prenatal diagnosis.

SUMMARY OF THE INVENTION

It is an aim of the present invention an isolation method for male cells in maternal biological tissue samples in the early stages of pregnancy for the diagnosis of X-linked diseases. The problem is solved with male-specific monoclonal antibodies against the Ribosomal Protein S4 Y-linked 1 (RPS4Y1), described here for the first time.

DRAWINGS

FIG. 1. Analysis of RPS4X and RPS4Y1 RT-PCR products. (A) Agarose gel electrophoresis showing RPS4X and RPS4Y1 cDNA bands amplified from male (Y) and female (X) peripheral blood mononuclear cells (PBMCs), chorionic villi, male HepG2 (cell culture Y) and female HEK293 cells (cell culture X). The bands of the GeneRuler 50 bp marker (M) are indicated on the left. (B) Bar graph showing the relative quantitation (RQ) of RPS4Y1 transcript in male PBMCs, chorionic villi and female HepG2 cells.

FIG. 2: Alignment of RPS4X (SEQ ID NO: 1) and RPS4Y1 (SEQ ID NO: 2) amino acid sequences. Amino acid differences between the two proteins are indicated by asterisks (*). The regions of RPS4Y1 protein selected as antigens for mice immunization are boxed and named Y1, Y2, Y3. X1, X2, X3 refer to the homologous regions of the homologous RPS4X protein, encoded by the X-linked gene RPS4X.

Figure 3:
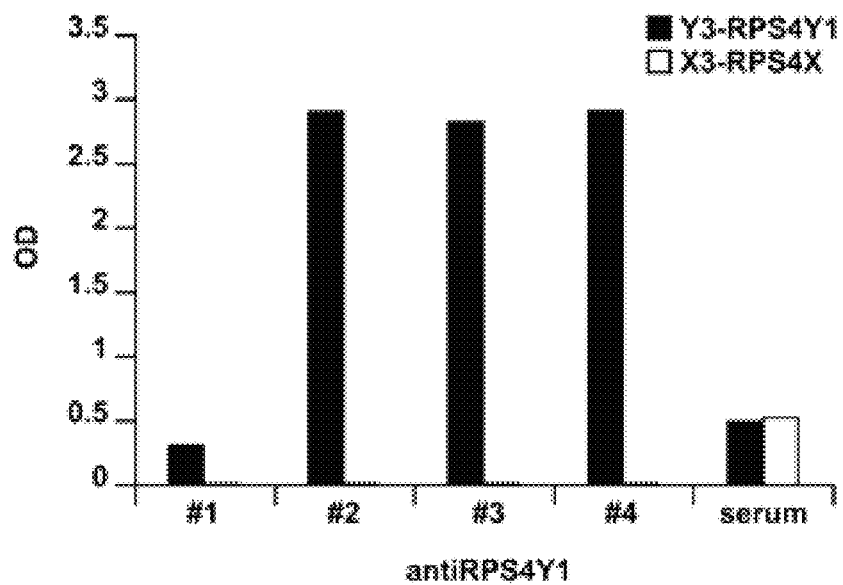

FIG. 3: Y3 antigen specificity of monoclonal antibodies. The bar graph shows the optical density (OD) from the ELISA assay (one out of three) performed using Y3 (black bar) or X3 (white bar) capture peptides and 2 μg/mL of anti-RPS4Y1 antibodies #1, #2, #3, #4 or mouse serum (x-axis).

Figure 4:
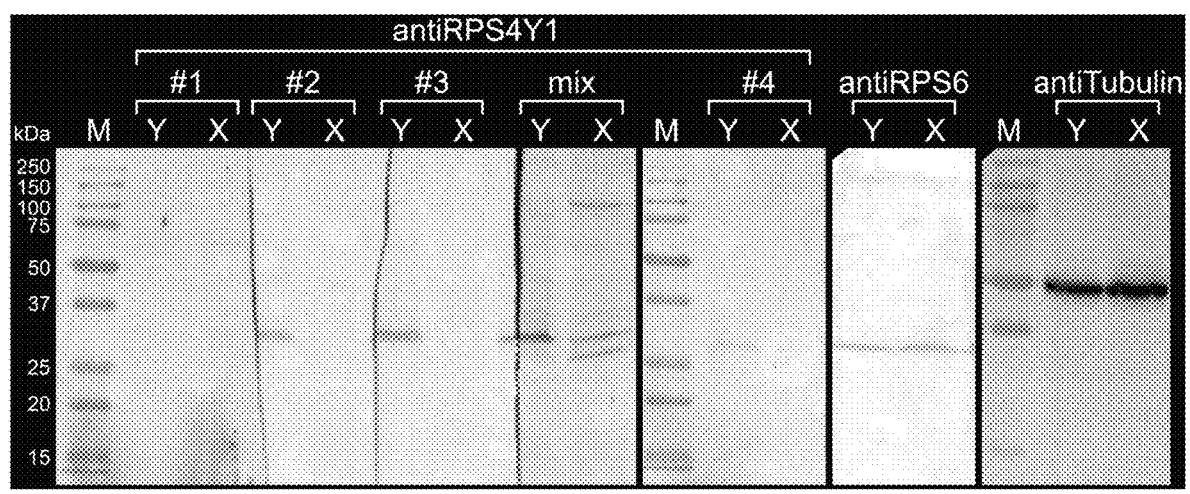

FIG. 4: mAbRPS4Y1 binding to the male RPS4Y1 protein. Representative results of SDS-PAGE and Western blotting (one out of three) performed on cell lysates of male HepG2 (Y) and female HEK293 (X) cells are showed. Anti-RPS4Y1 antibodies were tested individually (#1, #2, #3, #4) and in combination (mix). Anti-RPS46 and anti-tubulin antibodies were used as loading controls. The bands of the Precision Plus Protein marker (M) are indicated on the left.

Figure 5:
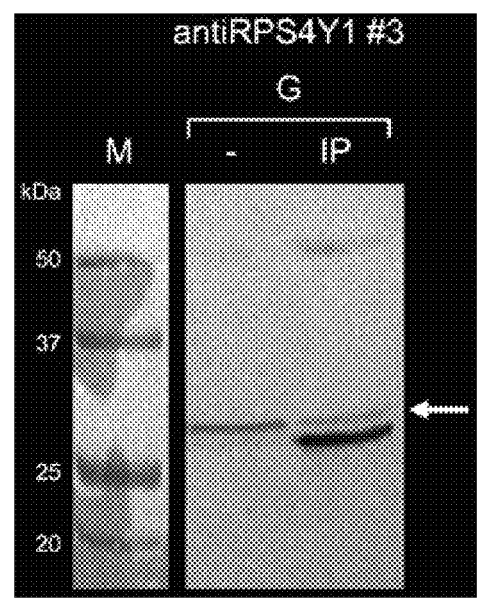

FIG. 5: mAbRPS4Y1#3 binding to the native RPS4Y1 protein. Representative results of immunoprecipitation experiments (one out of three) of mAbRPS4Y1#3 complex performed with magnetic beads coupled to protein G (G) are showed. Immunoprecipitated proteins (IP) and supernatants (—) were loaded and analyzed by SDS-PAGE and Western blotting. The arrow indicates the RPS4Y1 protein band.

Figure 6:
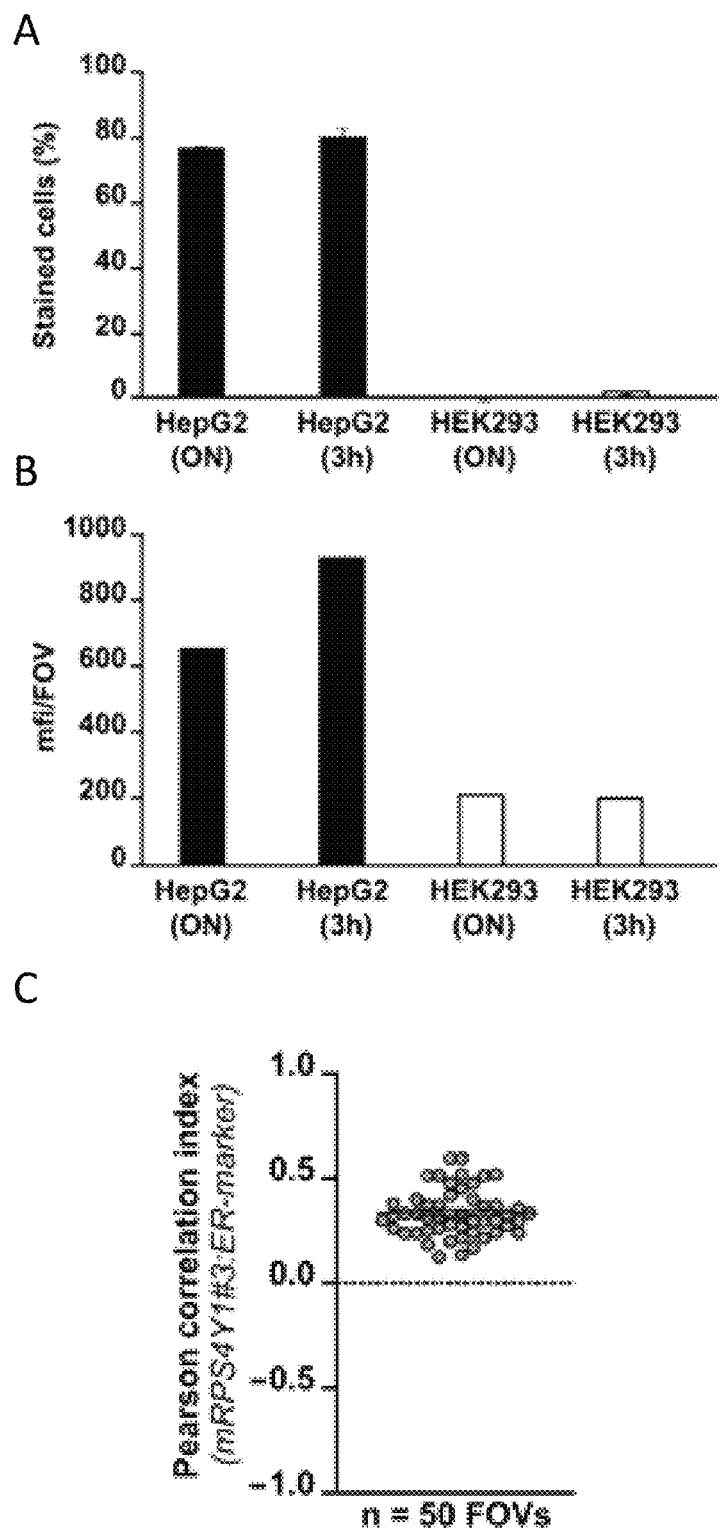

FIG. 6: mAbRPS4Y1#3 specificity for male cells. (A, B) Results of the digital imaging analysis of mAbRPS4Y1#3 staining reported as the percentage of positively stained cells relative to total cells (A) and the mean fluorescence intensity per field of view (mfi/FOV) (B). (C) Dot-plot showing the mean Pearson correlation index per FOV resulting from pixel by pixel digital analysis of mAbRPS4Y1#3 and ER-marker fluorescent signals performed on 50 FOVs from best-focus deconvolved Z plan at 100× magnification, with a mean number of 30 cells/FOV.

DESCRIPTION

As used in this application, the singular form "a", "an" and "the" include plural references unless the context clearly dictates otherwise. For example, the phrase "an antibody" also includes multiple antibodies.

As used herein, the term "comprising" means "including." Variations of the word "comprising", such as "comprise" and "comprises," have correspondingly varied meanings. Thus, for example, a sample "comprising" antibody A may consist exclusively of antibody A or may include one or more additional components (i.e. antibody B).

As used herein, the term "monoclonal antibody" or "mAb" or "monoclonal antibody composition" means a preparation of antibody molecules of single molecular composition, which displays a single binding specificity and affinity for a particular epitope.

As used herein, the term "hybridoma" refers to a cell produced by the fusion of an immortal cell (i.e. a multiple myeloma cell) and an antibody-producing cell (e.g. a B lymphocyte), which is capable of producing monoclonal antibodies of a single binding specificity.

As used herein, the terms "binding specifically" and "specifically binding" in reference to an antibody, antibody variant, antibody derivative, antigen binding fragment, and the like refers to its capacity to bind to a given target molecule preferentially over other non-target molecules.

As used herein, the term "subject" includes any animal including bovine, equine, ovine, primate, avian and rodent species. Hence, a "subject" may be a mammal such as, for example, a human or a non-human mammal.

In a first embodiment, it is here claimed an antibody or an antigen-binding fragment thereof, which specifically binds to RPS4Y1 protein, in an embodiment to human RPS4Y1 protein, which recognizes an epitope comprising sequence Y1 (SEQ ID NO: 3), and/or sequence Y2 (SEQ ID NO: 4) and/or sequence Y3 (SEQ ID NO: 5) of RPS4Y1, wherein

```
SEQ ID NO: 3 is
DVISIEKTGEHFRLVYD;

SEQ ID NO: 4 is
CKVRKITVGVKGIPHL;

SEQ ID NO: 5 is .
KVNDTVQIDLGTGKIINFIKFDT.
```

In an embodiment, said epitope comprises sequence Y3 (SEQ ID NO: 5) of RPS4Y1.

In an embodiment, said antibody is a monoclonal antibody.

In an embodiment, the monoclonal antibody is the monoclonal antibody #3, produced by the hydridoma having Deposit Designation PD22001, deposited with Interlab Cell Line Collection (ICLC), UOS Centro Risorse Biologiche, IRCCS Ospedale Policlinico San Martino, Largo Rosanna Benzi 10, 16132 Genoa, Italy on Jan. 25, 2022.

It forms a further aspect of the present invention an immunoconjugate comprising an antibody, or antigen-binding fragment thereof according to the present invention, coupled to a moiety.

In an embodiment, the moiety is a biologically active agent.

In an embodiment, the moiety is an immune-stimulating carrier molecule; nanoparticle; detectable label; drug; toxin; chelating agent; biotinylated moiety; tumor targeting agent; protein transduction domain or membrane permeating peptide; or part of a solid support.

In a further embodiment, it is here described a hybridoma secreting a monoclonal antibody having specific binding affinity for RPS4Y1 protein, wherein the hybridoma produces a monoclonal antibody that specifically binds to the epitope Y3 (SEQ ID NO: 5) on RPS4Y1 protein and does not significantly cross-react with other nucleotide bases, nor with RPS4X protein.

In an embodiment, the hybridoma has Deposit Designation PD22001, deposited with Interlab Cell Line Collection (ICLC), UOS Centro Risorse Biologiche, IRCCS Ospedale Policlinico San Martino, Largo Rosanna Benzi 10, 16132 Genoa, Italy on Jan. 25, 2022.

It forms a further aspect of the present invention a method for determining the presence RPS4Y1 protein in a biological specimen from a subject, comprising:
(a) obtaining a biological specimen from the subject;
(b) contacting the biological specimen with an antibody, an antigen-binding fragment thereof, or an immunoconjugate according to the present invention, and
(c) determining and/or quantifying binding of said antibody, antigen-binding fragment thereof, or immunoconjugate in the biological specimen of the subject.

In an embodiment, the biological specimen is selected from the group consisting of cells, tissue, blood, saliva, serum, plasma.

In an embodiment, the biological specimen is maternal plasma.

In an embodiment, it is disclosed a method of assessing sex of a foetus in a human subject, wherein said assessment is performed within three months of gestation, and said method comprises evaluating the presence of RPS4Y1 protein in a maternal plasma sample by contacting the same with an antibody, or antigen-binding fragment thereof, or an immunoconjugate according to the present invention, wherein the presence of RPS4Y1 protein in said sample is indicative of a male foetus.

Following are examples that illustrate procedures for practicing the invention.

These examples should not be construed as limiting.

Example 1: RPS4Y1 is a Marker of Male Cells

The alignment of complementary DNA (cDNA) sequences from the paralogue ribosomal protein S4 X-linked (RPS4X) and ribosomal protein S4 Y-linked 1 (RPS4Y1) genes (Reference Sequence NM_001007.5 and NM_001008.4, respectively) allowed the design of primers for the specific detection of the two RPS4 isoforms.

For this purpose, peripheral blood mononuclear cells (PBMCs) were isolated from 10 mL of fresh blood samples of healthy male and female donors using the Ficoll-Plaque Premium (GE Healthcare, Chicago, Ill., USA). Chorionic villi were obtained by standard clinical procedures. Reverse transcription polymerase chain reaction (RT-PCR) analysis on total RNA extracted from PBMCs of a male and a female donor showed an expected amplicon of 196 bp amplified by the RPS4X-primer couple in both male and female samples and an expected amplicon of 167 bp amplified by the RPS4Y1-primer couple only in the male sample (FIG. 1A). Direct sequencing of RT-PCR products confirmed the specificity of amplification and hence the unique expression of the RPS4Y1 gene in the male mononuclear cells. The same analyses performed on RNA samples from chorionic villi of a male and a female fetus and from human hepatoma (HepG2, Y) and human embryonic kidney (HEK293, X) cultured cells, used as unlimited source of biological material and derived respectively from a male and a female [22], confirmed the sex specific expression of the RPS4Y1 gene (FIG. 1A). This result was confirmed by quantitative PCR (qPCR) analysis that showed a reduced but equal expression of RPS4Y1 transcript in male villi and HepG2 cells compared to PBMCs (0.3 vs. 1 relative quantitation) (FIG. 1B).

Example 2: Selection of RPS4Y1-Antigen Peptides

The alignment of the reviewed amino acid (aa) sequences of RPS4X (SEQ ID NO: 1) and RPS4Y1 (SEQ ID NO: 2) proteins (UniProtKB P62701 and P22090, respectively) allowed the identification and localization of 19 aa differences between the RPS4X and the RPS4Y1 homologous proteins (FIG. 2).

SEQ ID NO: 1 is
MARGPKKHLKRVAAPKHWMLDKLTGVFAPRPSTGPHKLRECLPLIIFLR

NRLKYALTGDEVKKICMQRFIKIDGKVRTDITYPAGFMDVISIDKTGEN

FRLIYDTKGRFAVHRITPEEAKYKLCKVRKIFVGTKGIPHLVTHDARTI

RYPDPLIKVNDTIQIDLETGKITDFIKFDTGNLCMVTGGANLGRIGVIT

NRERHPGSFDVVHVKDANGNSFATRLSNIFVIGKGNKPWISLPRGKGIR

LTIAEERDKRLAAKQSSG.

SEQ ID NO: 2 is
MARGPKKHLKRVAAPKHWMLDKLTGVFAPRPSTGPHKLRECLPLIVFLR

NRLKYALTGDEVKKICMQRFIKIDGKVRVDVTYPAGFMDVISIEKTGEH

FRLVYDTKGRFAVHRITVEEAKYKLCKVRKITVGVKGIPHLVTHDARTI

RYPDPVIKVNDTVQIDLGTGKIINFIKFDTGNLCMVIGGANLGRVGVIT

NRERHPGSFDVVHVKDANGNSFATRLSNIFVIGNGNKPWISLPRGKGIR

LTVAEERDKRLATKQSSG.

Protein alignment of RPS4X and RPS4Y1 was performed using Clustal Omega tool (https://www.ebi.ac.uk/Tools/msa/clustalo/). Three small regions (Y1, Y2, Y3 of 17, 16 and 23 aa, SEQ ID NO: 3, SEQ ID NO: 4, SEQ ID NO: 5, respectively) with the highest number of aa specific for the RPS4Y1 protein (2, 3 and 4 respectively) were selected as antigens (FIG. 2). To improve immunogenicity, the three small linear peptides selected as antigens were conjugated to keyhole limpet hemocyanin (KLH) carrier protein and used as a pool preparation for mice immunization. KLH and Bovine Serum Albumin (BSA)-coupled peptides corresponding to aa 88-104, 124-139, 155-177 of RPS4X (X1, SEQ ID NO: 6=DVISIDKTGENFRLIYD; X2, SEQ ID NO. 7=CKVRKIFVGTKGIPHL; X3, SEQ ID NO: 8=KVNDTIQIDLETGKITDFIKFDT) and RPS4Y1 (Y1, Y2, Y3) were synthesized (Pepscan, Lelystad, The Netherlands). After screening for specific binding to the RPS4Y1 pool antigen, four antibody-producing hybridoma clones were selected and corresponding antiRPS4Y1 antibodies have been further analyzed.

Example 3: Anti-RPS4Y1 Antibodies are Specific for a RPS4Y1-Antigen Peptide and the RPS4Y1 Protein To evaluate the epitope binding of antiRPS4Y1 antibodies, enzyme-linked immuno-sorbent assay (ELISA) was performed on individual Y1 (SEQ ID NO: 3), Y2 (SEQ ID NO: 4), Y3 (SEQ ID NO: 5) antigen peptides. No reactivity was evidenced against the Y1 and Y2 peptides (data not shown). By contrast, three antiRPS4Y1 antibodies (#2, #3, #4) showed at each tested concentration (0.5-1-2 µg/mL) similar reactivity for the Y3 peptide (mean optical density, OD: 2.649, 2.775, 2.675 for antibodies #2, #3 and #4, respectively) and no reactivity for the counter-screened X3 (SEQ ID NO: 8) peptide (mean OD: 0.012, 0.016, 0.015 for antibodies #2, #3 and #4, respectively), thus suggesting a specific Y3-binding (FIG. 3).

The specificity of antiRPS4Y1 antibodies for the entire RPS4Y1 protein was also assessed.

HepG2 and HEK293 cell lines were obtained from the American Type Culture Collection (ATCC, Manassas, Va., USA). HepG2 and HEK293 cells were cultured in Dulbecco's Modified Eagle's Medium and Ham's F12 media (1:1, vol/vol), supplemented with 10% fetal calf serum. Glutamine (1%) and antibiotics (100 IU/mL penicillin and 100 µg/mL streptomycin) were added to both media. Cells were grown at 37° C. in a humidified atmosphere of 5% $CO_2$ and 95% air.

Total cell lysates extracted from male HepG2 and female HEK293 cultured cells were separated on sodium dodecyl sulphate-polyacrylamide gel electrophoresis (SDS-PAGE) and Western blotting was performed using antiRPS4Y1 antibodies, either single or in combination. As expected, a single band of approximately 30 kDa, corresponding to the molecular weight of the RPS4Y1 protein, was detected by mRPS4Y1 antibodies #2, #3, #4 in the male sample and not in the female one. This result confirmed the specificity of three monoclonal antibodies (mAbs) for the RPS4Y1 protein and the lack of cross-reactivity with the RPS4X homologous protein expressed both in male and in female cells (FIG. 4). The antiRPS4Y1 antibody #1, previously found unresponsive to the RPS4Y1 peptides by the ELISA assay, was used as negative control and confirmed lack of reaction with both male and female samples (FIG. 4). By contrast, antibodies against the housekeeping protein tubulin and the ribosomal protein S6 (RPS6), encoded by the RPS6 gene located in the autosomal chromosome 9 and component of the 40S subunit as RPS4X and RPS4Y1, were used as positive controls. As expected, two single bands corresponding to the molecular weight of tubulin (50 kDa) and RPS6 (28.7 kDa) proteins were evidenced in both male and female cell extracts (FIG. 4). The mixture of four antiRPS4Y1 antibodies evidenced a pattern of non-specific bands not only in male but also in female sample without the improvement of the specific signal in the male sample. Among the analyzed antiRPS4Y1 antibodies, the highest specific signal was observed with the antibody #3 (FIG. 4).

Immunoprecipitation analysis was further performed to assess the binding ability of antiRPS4Y1 antibody #3 to the native RPS4Y1 protein. Magnetic beads coupled to protein G with high affinity for mouse IgG were used to capture the antibody #3 bounded to the RPS4Y1 protein in HepG2 cell lysate. SDS-PAGE and Western blotting of immunoprecipitated (IP) samples and surnatants (—) showed three bands in IP: a high band and a low band corresponding respectively to 50 kDa-heavy and 25 kDa-light chains of immunoglobulins and an intermediate band corresponding to the 29.4 kDa RPS4Y1 protein (FIG. 5). This finding evidenced the ability of the antibody #3 to recognize the RPS4Y1 protein in its native conformation. The presence of the intermediate band in the protein-G supernatant, suggests that not all RPS4Y1 protein is trapped by the antibody.

Example 4: antiRPS4Y1 Antibody is Specific for Male Cells

Immunofluorescence analysis was performed to assess the ability of antiRPS4Y1 antibody #3 to detect male cells through the identification of the RPS4Y1 protein. Male HepG2 and female HEK293 cells were both incubated overnight (ON) at 4° C. and at room temperature for 3 h (3 h) with antiRPS4Y1 antibody #3. The almost sole staining of male HepG2 cells compared to female HEK293 cells was observed (76 vs. 0% and 80 vs. 2% for ON and 3 h incubation, respectively), thus suggesting the specific labelling of male cells (FIG. 6A). Moreover, the observed signal in HepG2 cells was specific since the mean intensity of mAbRPS4Y1 #3 was higher in male cells than in female ones (mean fluorescent intensity; 659 vs. 215 and 935 vs. 202 for ON and 3 h incubation, respectively) (FIG. 6B). Finally, subcellular imaging studies on HepG2 cells were performed. Analysis of RPS4Y1 localization at the level of cellular endoplasmic reticulum (ER) revealed as expected partial co-localization of mAbRPS4Y1 #3 and ER-marker calnexin (Pearson correlation index 0.4; mean from a total of 1500 analyzed HepG2 cells from n=50 independent field of view at high-resolution acquisition) (FIG. 6C).

References

1. Lo, Y. M.; Corbetta, N.; Chamberlain, P. F.; Rai, V.; Sargent, I. L.; Redman, C. W.; Wainscoat, J. S. Presence of fetal DNA in maternal plasma and serum. *Lancet* 1997, 350, 485-487.

2. Devaney, S. A.; Palomaki, G. E.; Scott, J. A.; Bianchi, D. W. Noninvasive fetal sex determination using cell-free fetal DNA: A systematic review and meta-analysis. *JAMA* 2011, 306, 627-636.

3. Mokari-Zadeh, N.; Mesbah-Namin, S. A. Evaluation of an Improved Non-invasive Fetal Sex Determination in Hemophilia A Patients. *J. Clin. Diagn. Res.* 2015, 9, GC01-GC04.

4. Bowman-Smart H., Savulescu J., Gyngell C., Mand C., Delatycki MB. Sex selection and non-invasive prenatal testing: A review of current practices, evidence, and ethical issues. *Prenat Diagn.* 2020, 40: 398-407.

5. Tsui, N. B.; Kadir, R. A.; Chan, K. C.; Chi, C.; Mellars, G.; Tuddenham, E. G.; Leung, T. Y.; Lau, T. K.; Chiu, R. W.; Lo, Y. M. Noninvasive prenatal diagnosis of hemophilia by microfluidics digital PCR analysis of maternal plasma DNA. *Blood* 2011, 117, 3684-3691.

6. Hudecova, I.; Jiang, P.; Davies, J.; Lo, Y. M. D.; Kadir, R. A.; Chiu, R. W. K. Noninvasive detection of F8 int22h-related inversions and sequence variants in maternal plasma of hemophilia carriers. *Blood* 2017, 130, 340-347.

7. Chen, C.; Sun, J.; Yang, Y.; Jiang, L.; Guo, F.; Zhu, Y.; Li, D.; Wu, R.; Lu, R.; Zhao, M.; et al. Noninvasive prenatal diagnosis of hemophilia A by a haplotype-based approach using cell-free fetal DNA. *Biotechniques* 2020, 68, 117-121.

8. Fiddler, M. Fetal Cell Based Prenatal Diagnosis: Perspectives on the Present and Future. *J. Clin. Med.* 2014, 3, 972-985.

9. Mergenthaler, S.; Babochkina, T.; Kiefer, V.; Lapaire, O.; Holzgreve, W.; Hahn, S. FISH analysis of all fetal nucleated cells in maternal whole blood: Improved specificity by the use of two Y-chromosome probes. *J. Histochem. Cytochem.* 2005, 53, 319-322.

10. Rezaei, M.; Winter, M.; Zander-Fox, D.; Whitehead, C.; Liebelt, J.; Warkiani, M. E.; Hardy, T.; Thierry, B. A Reappraisal of Circulating Fetal Cell Noninvasive Prenatal Testing. *Trends Biotechnol.* 2019; 37, 632-644.

11. Gänshirt-Ahlert, D.; Burschyk, M.; Garritsen, H. S.; Helmer, L.; Miny, P.; Horst, J.; Schneider, H. P.; Holzgreve, W. Magnetic cell sorting and the transferrin receptor as potential means of prenatal diagnosis from maternal blood. *Am. J. Obstet. Gynecol.* 1992, 166, 1350-1355.

12. Bianchi, D. W.; Zickwolf, G. K.; Yih, M. C.; Flint, A. F.; Geifman, O. H.; Erikson, M. S.; Williams, J. M. Erythroid-specific antibodies enhance detection of fetal nucleated erythrocytes in maternal blood. *Prenat. Diagn.* 1993, 13, 293-300.

13. Mavrou, A.; Kolialexi, A.; Antsaklis, A.; Korantzis, A.; Metaxotou, C. Identification of fetal nucleated red blood cells in the maternal circulation during pregnancy using anti-hemoglobin-epsilon antibody. *Fetal. Diagn. Ther.* 2003, 18, 309-313.

14. Sekizawa, A.; Purwosunu, Y.; Farina, A.; Okai, T.; Takabayashi, H.; Kita, M.; Yura, H.; Kitagawa, M. Development of noninvasive fetal DNA diagnosis from nucleated erythrocytes circulating in maternal blood. *Prenat. Diagn.* 2007, 27, 846-848.

15. Zimmermann, S.; Hollmann, C.; Stachelhaus, S. A. Unique monoclonal antibodies specifically bind surface structures on human fetal erythroid blood cells. *Exp. Cell. Res.* 2013, 319, 2700-2707.

16. Chang, L.; Zhu, X.; Li, R.; Wu, H.; Chen, W.; Chen, J.; Liu, H.; Li, S.; Liu, P. A novel method for noninvasive diagnosis of monogenic diseases from circulating fetal cells. *Prenat. Diagn.* 2020, 1-9, doi:10.1002/pd.5796.

17. Hatt, L.; Brinch, M.; Singh, R.; Moller, K.; Lauridsen, R. H.; Uldbjerg, N.; Huppertz, B.; Christensen, B.; Kølvraa, S. Characterization of fetal cells from the maternal circulation by microarray gene expression analysis—Could the extravillous trophoblasts be a target for future cell-based non-invasive prenatal diagnosis? *Fetal Diagn. Ther.* 2014, 35, 218-227.

18. Kølvraa, S.; Singh, R.; Normand, E. A.; Qdaisat, S.; van den Veyver, I. B.; Jackson, L.; Hatt, L.; Schelde, P.; Uldbjerg, N.; Vestergaard, E. M.; et al. Genome-wide copy number analysis on DNA from fetal cells isolated from the blood of pregnant women. *Prenat. Diagn.* 2016, 36, 1127-1134.

19. Brinch, M.; Hatt, L.; Singh, R.; Møller, K.; Sommer, S.; Uldbjerg, N.; Christensen, B.; Kølvraa, S. Identification of circulating fetal cell markers by microarray analysis. *Prenat. Diagn.* 2012, 32, 742-751.

20. Zinn, A. R.; Alagappan, R. K.; Brown, L. G.; Wool, I.; Page, D. C. Structure and function of ribosomal protein S4 genes on the human and mouse sex chromosomes. *Mol. Cell. Biol.* 1994, 14, 2485-2492.

21. Lopes, A. M.; Miguel, R. N.; Sargent, C. A.; Ellis, P. J.; Amorim, A.; Affara, N. A. The human RPS4 paralogue on Yq11.223 encodes a structurally conserved ribosomal protein and is preferentially expressed during spermatogenesis. *BMC Mol. Biol.* 2010, 11, 33.

22. Shah, K.; McCormack, C. E.; Bradbury, N. A. Do you know the sex of your cells? *Am. J. Physiol. Cell. Physiol.* 2014, 306, C3-C18.

The invention claimed is:

1. A non-invasive method for estimating gender of a foetus of a pregnant female within three months of gestation, said method comprising:
   (a) making available a maternal blood sample;
   (b) contacting said sample with monoclonal antibody #3 produced by the hybridoma having Deposit Designation PD22001, deposited with Interlab Cell Line Collection (ICLC), an antigen-binding fragment of monoclonal antibody #3, or an immunoconjugate of monoclonal antibody #3, that specifically recognizes RPS4Y1 protein, and
   (c) determining and/or quantifying binding of said antibody, antigen-binding fragment thereof, or immunoconjugate thereof in the sample from the subject,
   (d) estimating gender of said foetus based on said binding, wherein the presence in said sample of RPS4Y1 protein is indicative of a male foetus.

2. A method for determining the presence of RPS4Y1 protein in a biological specimen from a subject, comprising:
   (a) making available a biological specimen selected from the group consisting of cells, tissue, blood and saliva from the subject;
   (b) contacting said biological specimen with monoclonal antibody #3 produced by the hybridoma having Deposit Designation PD22001, deposited with Interlab Cell Line Collection (ICLC), an antigen-binding fragment of monoclonal antibody #3, or an immunoconjugate of monoclonal antibody #3, specifically recognizing RPS4Y1 protein, and (c) determining and/or quantifying binding of said antibody, antigen-binding fragment thereof, or immunoconjugate thereof to determine the presence of RPS4Y1 protein in the biological specimen of the subject.

3. The method according to claim 2, wherein the biological specimen is maternal blood.

4. The method according to claim 2, wherein said biological specimen is maternal blood obtained within three months of gestation, and the presence of RPS4Y1 protein in said sample is indicative of a male foetus.

* * * * *

SEQUENCE LISTING

<160> NUMBER OF SEQ ID NOS: 8

<210> SEQ ID NO 1
<211> LENGTH: 263
<212> TYPE: PRT
<213> ORGANISM: Homo sapiens
<220> FEATURE:
<221> NAME/KEY: misc_feature
<223> OTHER INFORMATION: RPS4X

<400> SEQUENCE: 1

```
Met Ala Arg Gly Pro Lys Lys His Leu Lys Arg Val Ala Ala Pro Lys
1               5                   10                  15

His Trp Met Leu Asp Lys Leu Thr Gly Val Phe Ala Pro Arg Pro Ser
            20                  25                  30

Thr Gly Pro His Lys Leu Arg Glu Cys Leu Pro Leu Ile Ile Phe Leu
        35                  40                  45

Arg Asn Arg Leu Lys Tyr Ala Leu Thr Gly Asp Glu Val Lys Lys Ile
    50                  55                  60

Cys Met Gln Arg Phe Ile Lys Ile Asp Gly Lys Val Arg Thr Asp Ile
65                  70                  75                  80

Thr Tyr Pro Ala Gly Phe Met Asp Val Ile Ser Ile Asp Lys Thr Gly
                85                  90                  95

Glu Asn Phe Arg Leu Ile Tyr Asp Thr Lys Gly Arg Phe Ala Val His
            100                 105                 110

Arg Ile Thr Pro Glu Glu Ala Lys Tyr Lys Leu Cys Lys Val Arg Lys
        115                 120                 125

Ile Phe Val Gly Thr Lys Gly Ile Pro His Leu Val Thr His Asp Ala
    130                 135                 140

Arg Thr Ile Arg Tyr Pro Asp Pro Leu Ile Lys Val Asn Asp Thr Ile
145                 150                 155                 160

Gln Ile Asp Leu Glu Thr Gly Lys Ile Thr Asp Phe Ile Lys Phe Asp
                165                 170                 175

Thr Gly Asn Leu Cys Met Val Thr Gly Gly Ala Asn Leu Gly Arg Ile
            180                 185                 190

Gly Val Ile Thr Asn Arg Glu Arg His Pro Gly Ser Phe Asp Val Val
        195                 200                 205

His Val Lys Asp Ala Asn Gly Asn Ser Phe Ala Thr Arg Leu Ser Asn
    210                 215                 220

Ile Phe Val Ile Gly Lys Gly Asn Lys Pro Trp Ile Ser Leu Pro Arg
225                 230                 235                 240

Gly Lys Gly Ile Arg Leu Thr Ile Ala Glu Glu Arg Asp Lys Arg Leu
                245                 250                 255

Ala Ala Lys Gln Ser Ser Gly
            260
```

<210> SEQ ID NO 2
<211> LENGTH: 263
<212> TYPE: PRT
<213> ORGANISM: Homo sapiens
<220> FEATURE:
<221> NAME/KEY: misc_feature
<223> OTHER INFORMATION: RPS4Y1

<400> SEQUENCE: 2

```
Met Ala Arg Gly Pro Lys Lys His Leu Lys Arg Val Ala Ala Pro Lys
1               5                   10                  15

His Trp Met Leu Asp Lys Leu Thr Gly Val Phe Ala Pro Arg Pro Ser
```

```
            20                  25                  30
Thr Gly Pro His Lys Leu Arg Glu Cys Leu Pro Leu Ile Val Phe Leu
            35                  40                  45

Arg Asn Arg Leu Lys Tyr Ala Leu Thr Gly Asp Glu Val Lys Lys Ile
        50                  55                  60

Cys Met Gln Arg Phe Ile Lys Ile Asp Gly Lys Val Arg Val Asp Val
65                  70                  75                  80

Thr Tyr Pro Ala Gly Phe Met Asp Val Ile Ser Ile Glu Lys Thr Gly
                85                  90                  95

Glu His Phe Arg Leu Val Tyr Asp Thr Lys Gly Arg Phe Ala Val His
            100                 105                 110

Arg Ile Thr Val Glu Glu Ala Lys Tyr Lys Leu Cys Lys Val Arg Lys
            115                 120                 125

Ile Thr Val Gly Val Lys Gly Ile Pro His Leu Val Thr His Asp Ala
        130                 135                 140

Arg Thr Ile Arg Tyr Pro Asp Pro Val Ile Lys Val Asn Asp Thr Val
145                 150                 155                 160

Gln Ile Asp Leu Gly Thr Gly Lys Ile Ile Asn Phe Ile Lys Phe Asp
                165                 170                 175

Thr Gly Asn Leu Cys Met Val Ile Gly Gly Ala Asn Leu Gly Arg Val
            180                 185                 190

Gly Val Ile Thr Asn Arg Glu Arg His Pro Gly Ser Phe Asp Val Val
        195                 200                 205

His Val Lys Asp Ala Asn Gly Asn Ser Phe Ala Thr Arg Leu Ser Asn
    210                 215                 220

Ile Phe Val Ile Gly Asn Gly Asn Lys Pro Trp Ile Ser Leu Pro Arg
225                 230                 235                 240

Gly Lys Gly Ile Arg Leu Thr Val Ala Glu Glu Arg Asp Lys Arg Leu
                245                 250                 255

Ala Thr Lys Gln Ser Ser Gly
            260

<210> SEQ ID NO 3
<211> LENGTH: 17
<212> TYPE: PRT
<213> ORGANISM: Homo sapiens
<220> FEATURE:
<221> NAME/KEY: misc_feature
<223> OTHER INFORMATION: Y1

<400> SEQUENCE: 3

Asp Val Ile Ser Ile Glu Lys Thr Gly Glu His Phe Arg Leu Val Tyr
1               5                   10                  15

Asp

<210> SEQ ID NO 4
<211> LENGTH: 16
<212> TYPE: PRT
<213> ORGANISM: Homo sapiens
<220> FEATURE:
<221> NAME/KEY: misc_feature
<223> OTHER INFORMATION: Y2

<400> SEQUENCE: 4

Cys Lys Val Arg Lys Ile Thr Val Gly Val Lys Gly Ile Pro His Leu
1               5                   10                  15

<210> SEQ ID NO 5
```

-continued

```
<211> LENGTH: 23
<212> TYPE: PRT
<213> ORGANISM: Homo sapiens
<220> FEATURE:
<221> NAME/KEY: misc_feature
<223> OTHER INFORMATION: Y3

<400> SEQUENCE: 5

Lys Val Asn Asp Thr Val Gln Ile Asp Leu Gly Thr Gly Lys Ile Ile
1               5                   10                  15

Asn Phe Ile Lys Phe Asp Thr
            20

<210> SEQ ID NO 6
<211> LENGTH: 17
<212> TYPE: PRT
<213> ORGANISM: Homo sapiens
<220> FEATURE:
<221> NAME/KEY: misc_feature
<223> OTHER INFORMATION: X1

<400> SEQUENCE: 6

Asp Val Ile Ser Ile Asp Lys Thr Gly Glu Asn Phe Arg Leu Ile Tyr
1               5                   10                  15

Asp

<210> SEQ ID NO 7
<211> LENGTH: 16
<212> TYPE: PRT
<213> ORGANISM: Homo sapiens
<220> FEATURE:
<221> NAME/KEY: misc_feature
<223> OTHER INFORMATION: X2

<400> SEQUENCE: 7

Cys Lys Val Arg Lys Ile Phe Val Gly Thr Lys Gly Ile Pro His Leu
1               5                   10                  15

<210> SEQ ID NO 8
<211> LENGTH: 23
<212> TYPE: PRT
<213> ORGANISM: Homo sapiens
<220> FEATURE:
<221> NAME/KEY: misc_feature
<223> OTHER INFORMATION: X3

<400> SEQUENCE: 8

Lys Val Asn Asp Thr Ile Gln Ile Asp Leu Glu Thr Gly Lys Ile Thr
1               5                   10                  15

Asp Phe Ile Lys Phe Asp Thr
            20
```